United States Patent [19]

Miller et al.

[11] Patent Number: 4,657,705
[45] Date of Patent: Apr. 14, 1987

[54] PROCESS FOR THE PREPARATION OF N-SUBSTITUTED AMINOMETHYLPHOSPHONIC ACIDS

[75] Inventors: William H. Miller, Glendale; David B. Reitz; Mitchell J. Pulwer, both of St. Louis, all of Mo.

[73] Assignee: Monsanto Company, St. Louis, Mo.

[21] Appl. No.: 778,839

[22] Filed: Sep. 23, 1985

[51] Int. Cl.$^4$ ................................................. C07F 9/38
[52] U.S. Cl. ........................ 260/502.5 F; 260/502.5 E
[58] Field of Search .................... 260/502.5 E, 502.5 F

[56] References Cited

U.S. PATENT DOCUMENTS

| | | | |
|---|---|---|---|
| 3,288,846 | 11/1966 | Irani et al. | 260/500 |
| 3,476,799 | 11/1969 | Vogt et al. | 260/502.5 E |
| 3,549,728 | 12/1970 | Balde et al. | 260/502.5 E |
| 3,567,768 | 3/1971 | Shen et al. | 260/502.5 |
| 3,832,393 | 8/1974 | Krueger et al. | 260/502.5 E |
| 3,927,080 | 12/1975 | Gaertner | 260/502.5 |
| 3,950,402 | 4/1976 | Franz | 260/502.5 |
| 3,956,370 | 5/1976 | Parry et al. | 260/502.5 F |
| 3,969,398 | 7/1976 | Hershman | 260/502.5 |
| 4,009,204 | 2/1977 | Krueger et al. | 260/502.5 |
| 4,065,491 | 12/1977 | Pfliegel et al. | 260/502.5 |
| 4,237,065 | 12/1980 | Ehrat | 260/502.5 |
| 4,243,591 | 1/1981 | Magin | 260/502.5 E |
| 4,442,041 | 4/1984 | Subramarian | 260/502.5 F |
| 4,491,548 | 1/1985 | Nagubandi | 260/502.5 F |
| 4,548,758 | 10/1985 | Nagubandi | 260/502.5 F |

FOREIGN PATENT DOCUMENTS

| | | |
|---|---|---|
| 0055695 | 7/1982 | European Pat. Off. |
| 2363634 | 6/1974 | Fed. Rep. of Germany ... 260/502.5 F |
| 47-1972112 | 1/1972 | Japan . |

Primary Examiner—J. E. Evans
Attorney, Agent, or Firm—Frank D. Shearin

[57] ABSTRACT

A process for the preparation of an N-substituted aminomethylphosphonic acid comprising reacting a substituted amine, urea or carbamate substrate compound with phosphorous acid and formaldehyde in an acidic medium.

5 Claims, No Drawings

PROCESS FOR THE PREPARATION OF N-SUBSTITUTED AMINOMETHYLPHOSPHONIC ACIDS

BACKGROUND OF THE INVENTION

This invention relates to the synthesis of N-substituted aminomethylphosphonic acids, and more particularly to an improved process in which an amide, urea or carbamate compound is reacted with phosphorous acid and formaldehyde in an acidic medium to produce an N-substituted aminomethylphosphonic acid.

N-substituted aminomethylphosphonic acids are useful intermediates in the preparation of various products, including sequestering agents and herbicides. Thus, for example, an N-alkyl-N-phosphonomethylamino acid, such as N-isopropyl-N-phosphonomethylglycine, can be dealkylated under alkaline conditions to the corresponding N-phosphonomethylamino acid using the method of the copending and coassigned application of Miller and Balthazor, Ser. No. 687,404 filed Dec. 28, 1984.

N-phosphonomethylglycine, known also by its common name glyphosate, is a highly effective and commercially important phytotoxicant useful in controlling a large variety of weeds. It is applied to the foliage of a very broad spectrum of annual and perennial grasses and broadleaf plants. Industrial uses include control of weeds along roadsides, waterways, transmission lines and in storage areas and other non-agricultural areas. Usually glyphosate is formulated into herbicidal compositions in the form of its various salts in solution, preferably water.

Because of its commercial importance, many processes for making glyphosate have been published. Processes are also known for the preparation of other phosphonomethylated amine compounds. In the former category, for example, is Gaertner U.S. Pat. No. 3,927,080 which describes the preparation of N-t-butyl-N-phosphonomethylglycine by reacting t-butylamine with a bromoacetate ester to produce an ester of N-t-butylglycine, and thereafter reacting the N-t-butylglycine ester with formaldehyde and a dialkyl phosphite to produce esters of N-t-butyl-N-phosphonomethylglycine. The latter product is hydrolyzed under acidic conditions to produce glyphosate.

European patent No. 00 55 695 discloses a process for splitting a 1-arylmethyl group from an N-1-arylalkyl-N-phosphonomethylglycine by hydrogenolytic cleavage. The glyphosate precursor is prepared by reaction of an N-1-arylalkylglycine with phosphorous acid and formaldehyde in an aqueous hydrochloric acid medium.

Pfliegel et al U.S. Pat. No. 4,065,491 describes the preparation of glyphosate directly by condensation of glycine, formaldehyde, and a dialkyl phosphite in an aqueous alkaline medium comprising sodium hydroxide.

Ehrat U.S. Pat. No. 4,237,065 describes a synthesis substantially similar to that disclosed in Pfliegel et al. However, Ehrat carries out the reaction using a tertiary amine base in an alcohol medium rather than the sodium hydroxide solution utilized by Pfliegel et al.

Irani and Moedritzer U.S. Pat. No. 3,288,846 also describes the reaction of other nitrogen compounds such as ammonia, or a primary or secondary amine, with an aldehyde or ketone and phosphorous acid to form an aminoalkylenephosphonic acid. However, unlike the processes disclosed by Pfliegel et al and Ehrat, the Irani process is carried out in an aqueous medium having a pH below about 4.

Shin et al U.S. Pat. No. 3,567,768 describes the preparation of an aminoalkylenephosphonic acid compound by reaction of a reactive nitrogenous material (i.e., a nitrogen containing or nitrogenous compound such as ammonia, a primary amine, or secondary amine), an aldehyde or ketone, and an excess of phosphorous acid. Where the nitrogenous reactant is ammonia or an ammonium salt, the product is the same as that prepared in accordance with the Krueger patent, discussed below. The exemplary disclosure of Shin describes a preparation in which phosphorous acid is premixed with ammonium chloride and water, and the resultant mixture is heated to reflux while formaldehyde is added thereto.

Japanese Pat. No. Sho 47[1972]-112 describes a method for the treatment of cellulose fibers with a solution which is prepared by the reaction of a nitrogen compound, phosphorous acid, and formalin. The nitrogen compound is one which contains two or more amino groups, such as for example, urea, thiourea, guanidine, or an alkyldiamide. However, the reference is concerned with enhancing the characteristics of the treated fiber and contains no disclosure of the structure of any product that may be formed by reaction of the aforesaid materials. Nor does the reference report any analytical work which might provide an indication of the structure of such product.

Krueger et al. U.S. Pat. No. 4,009,204 describes the preparation of nitrilo tris(methylenephosphonic acid) by reaction of an aliphatic amide with formaldehyde and a phosphorus trihalide. In the Krueger process, the amide substrate is preferably premixed with the aldehyde and the phosphorus trihalide added dropwise thereto. Alternatively, the aldehyde and phosphorus trihalide are premixed, and the acid amide slowly added to the latter premixture.

Various processes are known in the art for the preparation of amides, carbamates, and ureas. French Pat. No. 2,523,576 describes a method for preparing N-acyliminodiacetic acid by reaction of an unsubstituted amide with formaldehyde and carbon monoxide in the presence of a carbonylation catalyst. Provision of a method for conversion of the N-acyliminodiacetic acid to N-phosphonomethyliminodiacetic acid would establish an advantageous route to glyphosate, since Hershman U.S. Pat. No. 3,969,398 describes a process for preparation of glyphosate by oxidation of N-phosphonomethyliminodiacetic acid in the presence of activated carbon, and Franz U.S. Pat. No. 3,950,402 describes a similar process using a noble metal on carbon as a catalyst. The disclosure of Miller and Balthazor, Ser. No. 687,404 filed Dec. 28, 1984 describes the phosphonomethylation of N-isopropylglycine to N-isopropylglyphosate and conversion of the latter intermediate to glyphosate by dealkylation in an alkaline medium.

Other processes are available for the preparation of a wide variety of substituted and unsubstituted amides, carbamates, and ureas corresponding to the formula:

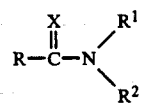

where typically R is hydrogen, alkyl, cycloalkyl, aryl, carboxyalkyl, alkoxy, aryloxy, or amino, $R^1$ and $R^2$ are independently selected from among hydrogen, alkyl, cycloalkyl, aryl, arylalkyl, and carboxyalkyl, and X is oxygen or sulfur.

The copending and coassigned application of Reitz, (Ser. No. 687,327 filed Dec. 28, 1984) describes a novel and advantageous method for the preparation of various amides.

SUMMARY OF THE INVENTION

Among the several objects of the present invention, therefore, may be noted the provision of an improved process for the preparation of N-substituted aminomethylphosphonic acid compounds; the provision of such a process which can be carried out without isolation of intermediates; the provision of such a process which produces products suitable for conversion to glyphosate or glyphosate derivatives, for example, by the process of Ser. No. 687,404 filed Dec. 28, 1984 or U.S. Pat. Nos. 3,950,402 or 3,969,398; and the provision of a process by which N-substituted aminomethylphosphonic acid compounds may be prepared from a variety of substituted amide, urea, or carbamate compounds; and, in particular, the provision of a process for producing N-substituted aminomethylphosphonic acids from substituted amides of the type produced in accordance with Reitz, Ser. No. 687,327 filed Dec. 28, 1984, and for the preparation of N-phosphonomethyliminodiacetic acid from N-acyliminodiacetic acids.

Briefly, therefore, the present invention is directed to a novel process for the preparation of an N-substituted aminomethylphosphonic acid comprising reacting a substituted amide, urea or carbamate substrate compound with phosphorous acid and formaldehyde in an acidic medium, the substrate compound represented by the formula:

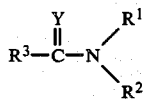

where Y is selected from the group consisting of oxygen or sulfur, $R^1$ and $R^2$ are independently selected from the group consisting of hydrogen, alkyl, aryl, arylalkyl, carboxyalkyl, and acyl, and at least one of $R^1$ and $R^3$ being a substituent other than hydrogen which is not hydrolyzable in the medium under the reaction condition, $R^3$ is selected from the group consisting of hydrogen, alkyl, aryl, arylalkyl, carboxyalkyl,

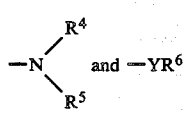

where Y is as defined above, $R^4$ and $R^5$ are independently selected from the group consisting of hydrogen, alkyl, aryl, arylalkyl, and carboxyalkyl, and $R^6$ is selected from the group consisting of alkyl, aryl, and arylalkyl, the N-substituted aminomethylphosphonic acid product represented by the formula:

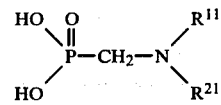

$R^{11}$ being selected from the group consisting of hydrogen and phosphonomethyl where $R^1$ is hydrogen or a group which is hydrolyzable under the reaction conditions, $R^{11}$ otherwise being identical to $R^1$, and $R^{21}$ being selected from the group consisting of hydrogen and phosphonomethyl where $R^2$ is hydrogen or a group hydrolyzable under the reaction conditions, $R^{21}$ otherwise being identical to $R^2$.

Other objects and features will be in part apparent and in part pointed out hereinafter.

DESCRIPTION OF THE PREFERRED EMBODIMENTS

In accordance with the invention, a novel process has been discovered by which substituted ureas, amides and carbamates, for example, amides of the type prepared in accordance with the aforesaid Reitz disclosure, can be phosphonomethylated to produce an N-substituted aminomethylphosphonic acid which can be converted to glyphosate by the process of Miller et al, Ser. No. 687,404 filed Dec. 28, 1984. By reaction of the amide, urea, or carbamate substrate with formaldehyde and phosphorous acid in an acidic medium, a phosphonomethyl group is substituted on the amine nitrogen in place of the carbonyl substituent. In the process of the invention, at least one of the substituents on the amine nitrogen is other than hydrogen and not subject to hydrolysis under the reaction conditions. In the context of this disclosure "not subject to hydrolysis" or "not hydrolyzable" more precisely means that the group in question is not subject to hydrolytic cleavage from the amine nitrogen under the reaction conditions but remains combined with the nitrogen in the reaction product. If the product of the reaction is a glyphosate precursor, that non-hydrolyzable substituent is preferably an alkyl group, such as, for example, isopropyl, which is subject to subsequent removal under alkaline conditions in accordance with the process of Ser. No. 687,404 filed Dec. 28, 1984. In another preferred application of the process of the invention, the substrate is an N-acyliminodiacetic acid, and the product is N-phosphonomethyliminodiacetic acid. As indicated above, the later compound is converted to glyphosate by contacting it with a molecular oxygen-containing gas in the presence of an activated carbon, as described in Hershman U.S. Pat. No. 3,969,398.

Generally, the substrate utilized in the process of the invention can be represented by the formula:

In this formula, $R^1$ and $R^2$ are independently selected from among hydrogen, alkyl, aryl, arylalkyl, carboxyalkyl, and acyl, at least one of $R^1$ and $R^2$ being a substituent other than hydrogen which is not hydrolyzable in the reaction medium under the reaction condition. Preferably, the substituent comprising $R^1$ and/or $R^2$ may contain up to about 8 carbon atoms. Among the alkyl groups which may comprise $R^1$ and/or $R^2$ are methyl, ethyl, n-propyl, isopropyl, n-butyl, secondary butyl, tertiary butyl, octyl, cyclohexyl, ethylcyclopentyl, and the like. Among the aryl groups which may constitute $R^1$ and/or $R^2$ are phenyl, tolyl, and diethylphenyl. The arylalkyl groups which may comprise $R^1$ and $R^2$ include benzyl, phenylethyl, naphthylmethyl, methylphenylethyl, and the like. The carboxyalkyl groups which may comprise $R^1$ and/or $R^2$ include, for example, carboxymethyl, carboxyethyl, carboxypropyl, carboxylbutyl, carboxypentyl, and carboxyheptyl. Exemplary acyl groups which may comprise $R^1$ and/or $R^2$ include formyl, acetyl, benzoyl, propanoyl, and methylbenzoyl.

Substituent $R^3$ in the substrate compound is selected from among hydrogen, alkyl, aryl, carboxyalkyl and various amine, alkoxy, and aryloxy radicals. Generally, $R^3$ may contain up to about 8 carbon atoms. Because the substituent of which it is a part is removed hydrolytically, it is feasible for $R^3$ to contain significantly more than 8 carbon atoms, but normally this would serve no useful purpose. Where $R^3$ is an alkyl, aryl or carboxyalkyl group, it may typically comprise any of the substituents which may comprise $R^1$ and/or $R^2$ as listed above. Where $R^3$ is an amine, alkoxy or aryloxy group, it corresponds to the formula:

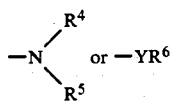

where Y is as defined above, $R^4$ and $R^5$ are independently selected from among hydrogen, alkyl, aryl, arylalkyl, and carboxyalkyl, and $R^6$ is selected from among alkyl, aryl, and arylalkyl. Here also, $R^1$ and $R^2$ may be typically selected from among the alkyl, aryl, and carboxyalkyl groups, and $R^6$ may be selected from among the alkyl, aryl, and arylalkyl groups, listed above with respect to $R^1$ and $R^2$.

In the structural formula for the substrate compound, Y comprises either oxygen or sulfur, but is preferably oxygen.

In carrying out the process of the invention, it is preferred that the substrate be initially dissolved or dispersed in an aqueous acidic medium, such as, for example, hydrochloric acid, hydrobromic acid or sulfuric acid, the acid typically having a strength of 10–25% by weight. Hydrochloric acid at a strength of between about 15% and about 25% by weight is a particularly effective medium for carrying out the reaction. After the substrate has been dissolved or dispersed in the aqueous acidic medium, the resultant mixture is preferably heated, for example, to a temperature of 70° C. to 120° C. Advantageously, the system may be heated to reflux temperature, which in the case of 20% hydrochloric acid is typically in the range of 105° C.–110° C. As noted, reaction with phosphorous acid and formaldehyde may then proceed without isolation of any intermediate.

The process may be initiated by heating a mixture of substrate and phosphorous acid in a hydrochloric, hydrobromic or sulfuric acid medium. In an alternative procedure, the substrate may be mixed with a phosphorus trihalide, such as phosphorus trichloride or phosphorus tribromide, and water, the phosphorus trihalide reacting with the water to produce a mixture of phosphorous acid and either hydrochloric or hydrobromic acid. Whenever and in whatever form it is introduced into the reaction system, phosphorous acid should be charged in a proportion of at least about one equivalent per equivalent of substrate. Where the substrate is a urea having two reactive nitrogens and/or when geminal diphosphonomethylation is desired, the stoichiometric requirements for phosphorous acid increase proportionately. Whatever the stoichiometry, about 10% excess of phosphorous acid is preferably charged.

The temperature of the system is maintained at at least about 90° C., more preferably at just below atmospheric reflux while formaldehyde is added slowly thereto. Formaldehyde may be added in any of its various monomeric or oligomeric forms, but is most conveniently added as formalin. Typically, addition of formaldehyde may be carried out over a period of at least 0.5 hour, after which the temperature is preferably maintained at reflux for at least 2 hours. Formaldehyde should be added in an amount of at least one mole per mole of substrate. Formaldehyde stoichiometry is governed by the same considerations discussed above with respect to phosphorous acid. Complete conversion of the substrate is promoted by introducing formaldehyde into the reaction zone in an approximate 20% excess based on the stoichiometric requirement.

Generally, the product of the reaction can be represented by the formula:

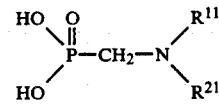

where $R^1$ is hydrogen or a group which is hydrolyzable under the reaction conditions, $R^{11}$ is either hydrogen or phosphonomethyl. Otherwise $R^{11}$ is the same as $R^1$. Similarly, when $R^2$ is hydrogen or a group that is hydrolyzable under the reaction conditions, $R^{21}$ is either hydrogen or phosphonomethyl. Otherwise $R^{21}$ is the same as $R^2$.

In the case where $R^{11}$ or $R^{21}$ is hydrogen or a hydrolytically cleavable group, the extent of phosphonomethylation is dependent on the reactant ratios and the reaction conditions. Using about one mole of phosphorous acid and one mole of formaldehyde per mole of a substrate having a single reactive nitrogen, the monophosphonomethylated product predominates. By essentially doubling the relative proportions of phosphorous acid and formaldehyde a geminally bisphosphonomethylated product predominates. Similar considerations apply where the substrate is a urea and both nitrogens are reactive, i.e., at least one of $R^4$ and $R^5$ is hydrogen, and at least one of $R^1$ and $R^2$ is hydrogen or a hydrolytically cleavable group. However, where there are two reactive nitrogens with a total of three or four reactive sites, kinetic (and possibly equilibrium) relationships become more complex and the products of reaction may comprise a variegated mixture.

After the reaction is completed, the product may be recovered if desired by conventional techniques such as, for example, crystallization. However, where the N-substituted aminomethylphosphonic acid is prepared as an intermediate for glyphosate, such conversion to glyphosate can be carried out directly, without recovery of the N-substituted N-phosphonomethylglycine from the reaction medium.

Where the process of the invention is used in the synthesis of glyphosate, the initial substrate is preferably an amine in which one of $R^1$ and $R^2$ is an alkyl substituent and the other is carboxymethyl. Most preferably, the alkyl substituent is isopropyl and the $R^3$ substituent is methyl. In this instance, the product of the reaction is N-isopropyl-N-phosphonomethylglycine, which is converted in very high yield to glyphosate in accordance with the alkaline medium dealkylation process described in the aforesaid application of Miller et al, Ser. No. 687,404 filed Dec. 28, 1984.

The following examples illustrate the invention:

EXAMPLE 1

A 3-necked 50 ml flask was fitted with a condenser, addition funnel, thermometer, and magnetic stir bar. N-Acetyl-N-isopropylglycine (2.55 g; 16.0 mmol), phosphorous acid (1.38 g; 16.8 mmol) and aqueous 20% by weight hydrochloric acid solution (10 ml) were introduced into the flask. The resulting mixture dissolved quickly, and was heated to a temperature of 106° C. over a period of 5 minutes. When this temperature range was reached, addition of a 37% by weight formaldehyde solution in water was begun. Over a period of about 0.5 hour, 1.56 g (19.2 mmol) of formaldehyde was added to the reaction mixture. After addition of the formaldehyde was complete, the reaction mixture was maintained at 106° C.–108° C. for an additional 3.5 hour. All volatiles were removed at reduced pressure and the residue was purified by ion-exchange chromatography (Dowex 50X8-400). The isolated product was a glassy solid (2.85 g; 84.4%) which was determined by NMR analysis to be substantially pure N-isopropyl-N-phosphonomethylglycine.

EXAMPLE 2

A crude reaction mixture of N-acetyliminodiacetic acid was prepared from acetamide (5.90 g; 0.10 mol)) by the process described in French Pat. No. 2,523,576. This crude product was dissolved in a 20% aqueous hydrochloric acid solution and the resulting mixture was added to a 250 ml 3-necked flask equipped with an addition funnel and thermometer. Phosphorous acid (8.61 g; 0.105 mol) was added and the solution was heated to a temperature of 106° C.–107° C. When this temperature had been reached, formaldehyde (8.23 g of a 44% aqueous solution; 0.212 mole) was added to the mixture in the flask over a period of 30 minutes. After addition of formaldehyde was complete, the temperature was maintained at 106°–107° C. for an additional period of 3.5 hour. The reaction mixture was concentrated under reduced pressure and a precipitate formed. The product was collected by filtration to yield 14.4 g of N-phosphonomethyliminodiacetic acid (63% yield based on the starting amount of acetamide).

EXAMPLE 3

A 50 ml 3-necked flask was fitted with a condenser, addition funnel, thermometer, and magnetic stir bar. Ethyl N-ethylcarbamate (3.0 g; 25.6 mmol) was introduced into the flask, after which phosphorous acid (4.4 g; 53.8 mmol) and a 30% hydrochloric acid solution (10 ml) were added and the solution heated quickly, i.e., over a period of 5-10 minutes, to a temperature of 105°–108° C. Formaldehyde (5.0 g of a 37% solution; 61.5 mmol) was added from the addition funnel over the course of an hour. After addition of the formaldehyde was completed, the reaction solution was maintained at 105° to 108° C. for an additional period of 15 minutes. Volatiles generated during this time were periodically distilled off in order to maintain the temperature at near 108° C. After the reaction period was completed, all volatiles were removed at reduced pressure and the residual material was purified by ion-exchange chromatography. Isolated from the chromatography was 4.74 g (79.4% yield) of N,N-bis-(phosphonomethyl)ethylamine.

EXAMPLE 4

Using a procedure essentially similar to that described in Example 3, N,N-dimethylaminomethylphosphonic acid (5.05 g; 70.4% yield) was produced by reaction of phosphorous acid and formaldehyde with N,N,N',N'-tetramethylurea (3.0 g; 25.8 mmole).

In view of the above, it will be seen that the several objects of the invention are achieved and other advantageous results attained.

As various changes could be made in the above methods without departing from the scope of the invention, it is intended that all matter contained in the above description or shown in the accompanying drawings shall be interpreted as illustrative and not in a limiting sense.

What is claimed is:

1. A process for the preparation of an N-substituted aminomethylphosphonic acid represented by the formula:

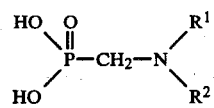

wherein $R^1$ is alkyl or carboxyalkyl, and $R^2$ is carboxyalkyl, which comprises:

preparing a mixture of an aqueous acidic medium comprising phosphorous acid; an acid selected from the group consisting of sulfuric acid, hydrochloric acid and hydrobromic acid; and a substituted substrate compound represented by the formula:

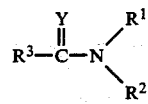

wherein $R^1$ and $R^2$ are as defined above, Y is oxygen or sulfur, and $R^3$ is selected from the group consisting of alkyl and carboxyalkyl;

heating the mixture to a temperature between about 70° C. and 120° C.; and thereafter slowly adding formaldehyde to the mixture.

2. A process as set forth in claim 1 wherein $R^1$ is isopropyl.

3. A process as set forth in claim 2 where $R^3$ is methyl.

4. A process as set forth in claim 3 further comprising dealkylating the N-isopropyl-N-phosphonomethylglycine compound product in the presence of base to produce a salt of glyphosate.

5. A process as set forth in claim 1 wherein said mixture is maintained at a temperature of approximately atmospheric reflux temperature during the addition of formaldehyde.

* * * * *